(12) United States Patent
Shimada et al.

(10) Patent No.: US 10,478,671 B2
(45) Date of Patent: Nov. 19, 2019

(54) AEROBIC EXERCISE ASSISTANCE APPARATUS

(71) Applicants: INTER REHA CO., LTD., Tokyo (JP); NATIONAL CENTER FOR GERIATRICS AND GERONTOLOGY, Aichi (JP)

(72) Inventors: Hiroyuki Shimada, Aichi (JP); Hajime Noguchi, Tokyo (JP)

(73) Assignees: INTER REHA CO., LTD., Tokyo (JP); NATIONAL CENTER FOR GERIATRICS AND GERONTOLOGY, Aichi (JP)

( * ) Notice: Subject to any disclaimer, the term of this patent is extended or adjusted under 35 U.S.C. 154(b) by 142 days.

(21) Appl. No.: 15/737,181

(22) PCT Filed: Oct. 2, 2015

(86) PCT No.: PCT/JP2015/078108
§ 371 (c)(1),
(2) Date: Dec. 15, 2017

(87) PCT Pub. No.: WO2016/203664
PCT Pub. Date: Dec. 22, 2016

(65) Prior Publication Data
US 2018/0169476 A1 Jun. 21, 2018

(30) Foreign Application Priority Data

Jun. 17, 2015 (JP) ................................. 2015-122354
Aug. 20, 2015 (JP) ................................. 2015-162930

(51) Int. Cl.
*A63B 24/00* (2006.01)
*A63B 22/06* (2006.01)
(Continued)

(52) U.S. Cl.
CPC ...... *A63B 24/0087* (2013.01); *A63B 22/0235* (2013.01); *A63B 22/06* (2013.01);
(Continued)

(58) Field of Classification Search
CPC ............ A63B 24/0087; A63B 22/0235; A63B 24/0059; A63B 22/06; A63B 2024/0093; G16H 10/20; G16H 20/30
See application file for complete search history.

(56) References Cited

U.S. PATENT DOCUMENTS

2011/0112855 A1* 5/2011 Chen .................. A63B 24/0062
705/2
2014/0011176 A1* 1/2014 Mayumi .................. G09B 5/14
434/336
(Continued)

FOREIGN PATENT DOCUMENTS

JP 2005192647 A 7/2005
JP 2011523087 A 8/2011
(Continued)

OTHER PUBLICATIONS

"Around the world!! Running quiz," https://ja.wikipedia.org/wiki/ 世界一周!!ランニングクイズ, with English translation, last updated Saturday, Jun. 2, 2018, 5 pages.

*Primary Examiner* — Sundhara M Ganesan
(74) *Attorney, Agent, or Firm* — Muncy, Geissler, Olds & Lowe, PC (57) ABSTRACT

An aerobic exercise assistance apparatus 1 includes an input/output unit 131 that, under control by a control unit, gives a user a question and accepts an input of an answer from the user to the question while the user performs the aerobic exercise. The control unit controls the load application driving unit 110, 120 to change the load applied by the load application driving unit 110, 120, based on a correct (Continued)

answer ratio of the user for the question and timing of the answer to the question by the user.

8 Claims, 6 Drawing Sheets

(51) Int. Cl.
*A63B 22/02* (2006.01)
*G16H 10/20* (2018.01)
*G16H 20/30* (2018.01)

(52) U.S. Cl.
CPC ......... *A63B 24/0059* (2013.01); *G16H 10/20* (2018.01); *A63B 2024/0093* (2013.01); *G16H 20/30* (2018.01)

(56) References Cited

U.S. PATENT DOCUMENTS

| | | | |
|---|---|---|---|
| 2014/0011177 A1* | 1/2014 | Mayumi | G09B 7/00 434/336 |
| 2015/0196836 A1* | 7/2015 | Drendel | A63F 3/00028 273/259 |
| 2018/0360340 A1* | 12/2018 | Rehse | A63B 24/0062 |

FOREIGN PATENT DOCUMENTS

| | | |
|---|---|---|
| WO | WO0078413 A1 | 12/2000 |
| WO | WO2009069756 A1 | 6/2009 |
| WO | WO2009137663 A1 | 11/2009 |

\* cited by examiner

AEROBIC EXERCISE ASSISTANCE APPARATUS

TECHNICAL FIELD

The present invention relates to an aerobic exercise assistance apparatus such as an ergometer and a treadmill that provides a loaded exercise for cognitive function in which a user thinks while performing an aerobic exercise, to thereby increase cerebral blood flow.

BACKGROUND ART

A cognitive function disorder improvement system for improving cognitive function decline due to dementia has been known (for example, Patent Document 1). The cognitive function disorder improvement system employs an ergometer and a training method, which is a combination of a biofeedback therapy and an exercise therapy, to improve cognitive function decline due to dementia.

Patent Document 1: Japanese Unexamined Patent Application Publication No. 2005-192647

DISCLOSURE OF THE INVENTION

Problems to be Solved by the Invention

However, in the conventional cognitive function disorder improvement system, cognitive function decline is determined according to, for example, the Hasegawa dementia rating scale-revised (HDS-R); however, aggressive improvement in cerebral blood flow is not effectively made.

An objective of the present invention is to provide an aerobic exercise assistance apparatus that provides a loaded exercise for cognitive function by aggressively making a user think during an aerobic exercise to thereby increase cerebral blood flow and suppress cognitive function decline.

Means for Solving the Problems

The present invention relates to an aerobic exercise assistance apparatus including: a load application driving unit that is driven to apply a load continuously to a part or an entirety of a user's body against a movement of the part or the entirety of the body, in order to cause a user perform an aerobic exercise by continuously moving the part or the entirety of the body; a control unit that controls the load application driving unit to change the load applied by the load application driving unit; and an input/output unit that, under control by the control unit, gives the user a question and accepts an input of an answer from the user to the question while the user performs the aerobic exercise, in which the control unit controls the load application driving unit to change the load applied by the load application driving unit, based on a correct answer ratio of the user for the question and timing of the answer to the question by the user.

In addition, it is preferable that the load application driving unit and the control unit constitute an ergometer. In addition, it is preferable that the control unit changes the load applied by the load application driving unit immediately after the user answers the question at a predetermined correct answer ratio.

In addition, it is preferable that the question comprises a question set for loaded exercise for cognitive function that causes the user perform a loaded exercise for cognitive function to thereby increase cerebral blood flow of the user.

In addition, it is preferable that a seat portion that allows the user to perform the aerobic exercise in a seated position is provided, the seat portion having an armrest. In addition, it is preferable that a fingerprint authentication device that can identify a predetermined user is provided.

In addition, it is preferable that a seat portion that allows the user to perform the aerobic exercise in a seated position is provided, the seat portion having a switching member that is supported by a slide rail so as to be movable with respect to the slide rail and switches between a movable state and a fixed state with respect to the slide rail.

Effects of the Invention

According to the present invention, an aerobic exercise assistance apparatus is provided that provides a loaded exercise for cognitive function by aggressively making a user think during an aerobic exercise to thereby increase cerebral blood flow and suppress cognitive function decline.

PREFERRED MODE FOR CARRYING OUT THE INVENTION

An embodiment of the present invention is described hereinafter based on FIGS. 1 to 6B. The aerobic exercise assistance apparatus 1 is composed of an ergometer and includes: a main body front part 10; a main body rear part 50; a pedal driving unit 110 and an electronic device 120 as the load application driving unit; a touch screen 131 as the input/output unit; an operation control device 135; and a seat unit 510. The pedal driving unit 110 is supported by the main body front part 10. The electronic device 120 is stored in the main body front part 10. The seat unit 510 is disposed in an upper portion of the main body rear part 50. The main body rear part 50 is supported by a slide rail 101 fixed onto the main body front part 10. The main body rear part 50 was fixed to the main body front part 10. The main body rear part 50 can be guided by the slide rail 101 to be spaced apart from/approach to the main body front part 10, in other words, can move to right/left in FIG. 1. The upper portion of the main body front part 10 includes an upward extending part 102 that extends upward, and an extended end portion of the upward extending part 102 is constituted of a horizontal table-like part 103.

Figure 1:
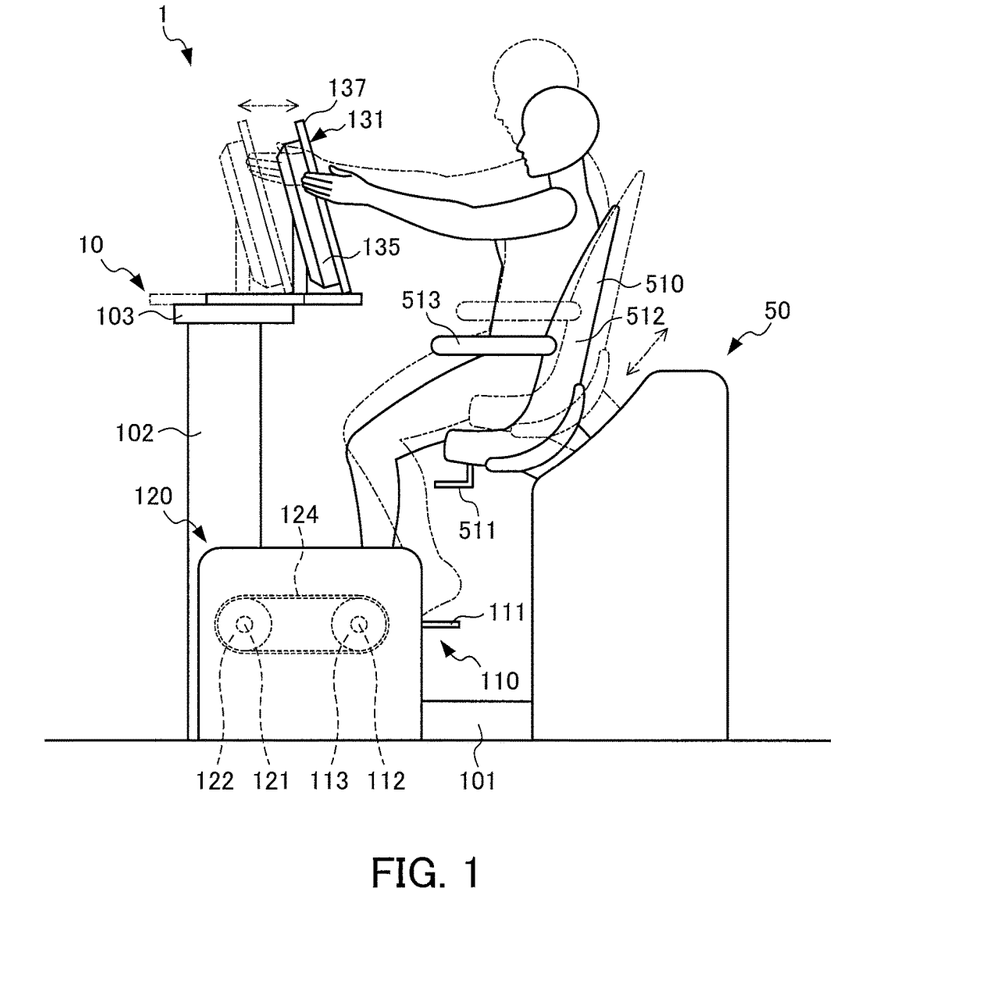
FIG. 1 is a schematic view illustrating an aerobic exercise assistance apparatus 1 according to an embodiment of the present invention.

A fingerprint authentication device (not illustrated) is provided on an upper face of the table-like part 103, more on a side of the main body rear part 50 than the touch screen 131. The fingerprint authentication device (not illustrated) is electrically connected to a control device unit 136 and can identify a predetermined user by his/her fingerprint being in contact therewith. In a case in which a plurality of users use the aerobic exercise assistance apparatus 1, this can prevent errors such as applying a "level" of the predetermined user having already used the aerobic exercise assistance apparatus 1 to other users.

The sheet unit 510 disposed in the upper portion of the main body rear part 50 is movable vertically with respect to the main body rear part 50. More specifically, a slide rail (not illustrated) is provided in the upper portion of the main body rear part 50 and the seat unit 510 is supported by the slide rail (not illustrated). The sheet unit 510 can be guided by the slide rail (not illustrated) to move to a lower front side/upper rear side, that is, to a lower left side/upper left side in FIG. 1. In other words, when a user trying to pedal a pedal 111 (described later) of the pedal driving unit 110 finds him/herself too far away from the pedal 111, the user moves the seat unit 510 along the slide rail (not illustrated) to the lower left side in FIG. 1 and moves the main body rear part 50 along the slide rail 101 to the left side in FIG. 1 to thereby bring the seat unit 510 closer to the pedal 111. On the contrary, when a user trying to pedal the pedal 111 finds him/herself too close to the pedal 111, the user moves the seat unit 510 along the slide rail (not illustrated) to the upper right side in FIG. 1 and moves the main body rear part 50 along the slide rail 101 to the right side in FIG. 1 to thereby separate the seat unit 510 from the pedal 111.

The seat unit 510 includes a slide lock lever 511 as the switching member. The slide lock lever 511 is configured to switch between movable and fixed states of the seat unit 510 with respect to the slide rail such that when the user sitting on the seat unit 510 grips and pulls the slide lock lever 511, the seat unit 510 becomes movable with respect to the slide rail (not illustrated), and when the user releases the slide lock lever 511, the seat unit 510 is locked with respect to the slide rail (not illustrated).

The seat unit 510 is configured to allow a user to perform the aerobic exercise of pedaling the pedal 111 in a seated position. The seat unit 510 includes a seat component 512 and an armrest 513. The seat component 512 is connected to the slide rail (not illustrated) provided in the main body rear part 50. The armrest 513 extends forward from the seat component 512 of the seat unit 510 when the user pedals the pedal 111. A first end portion of the armrest 513 is pivotally supported by the seat component 512. The armrest 513 thus pivots to be in a state of extending upward from the seat component 512 when the user is going to be seated on the seat component 512. After the user is seated, the armrest 513 pivots in a reverse direction and in a state of extending forward from the seat component 512. Such a state prevents the user seated on the seat component 512 from falling.

The pedal driving unit 110 includes a pair of pedals 111, a pedal shaft 112, and a pedal pulley 113. It should be noted that only one pedal 111 is illustrated in FIG. 1. The pair of pedals 111 is supported by the main body front part 10 to be pivotable with respect to the main body front part 10 about the pedal shaft 112. The pedal pulley 113 is fixed to the pedal shaft 112 so as to be pivotable integrally with the pedal shaft 112. The electronic device 120 includes a rotational shaft 121, a rotational shaft pulley 122, and an electric motor generator 125 (refer to FIG. 2). An endless belt 124 is stretched around the pedal pulley 113 and the rotational shaft pulley 122.

Figure 2:
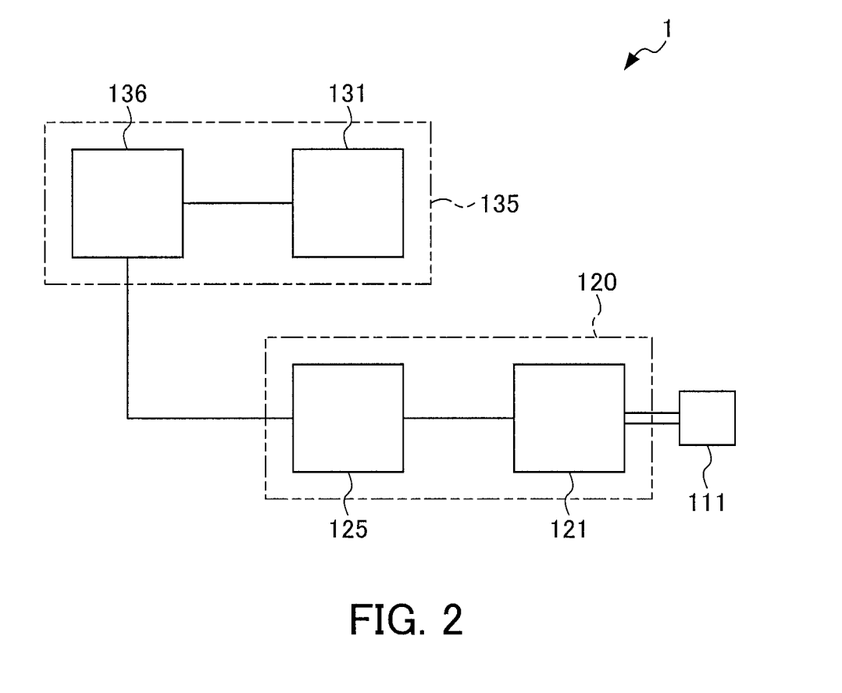
FIG. 2 is a block diagram illustrating the aerobic exercise assistance apparatus 1 according to an embodiment of the present invention.

As illustrated in FIG. 2, the electric motor generator 125 coupled to the rotational shaft 121 via a drive coupling part such as a gear in the electronic device 120 is electrically connected to an operation control device 135. The operation control device 135 is composed of a monitor-integrated computer including: the control device unit 136 as the control unit; and the touch screen 131 as the input/output unit electrically connected to the control device unit 136. The control device unit 136 includes: a storage unit (RAM and ROM (not illustrated)) that stores programs and information such as questions described later; and a calculation unit (CPU (not illustrated)) that performs arithmetic processing based on the information stored in the storage unit. The touch screen 131 is used for outputting by displaying questions to be provided to the user, and allowing the user to input various setting information and answers the questions provided. The operation control device 135 controls operation of the electronic device 120 based on the setting information and the answers to the question input through the touch screen 131.

The operation control device 135 including the touch screen 131 is supported by a slide rail (not illustrated) provided on the horizontal table-like part 103 of the upward extending part 102 of the main body front part 10. The operation control device 135 can be guided by the slide rail (not illustrated) to move to a front side (left side in FIG. 1) and to a rear side (right side in FIG. 1). In other words, when the user finds him/herself too far away from the touch screen 131, the user moves the operation control device 135 along the slide rail (not illustrated) to the right side in FIG. 1 to thereby bring the touch screen 131 closer to the user being seated on the set unit 510. On the contrary, when the user finds him/herself too close to the touch screen 131, the user moves the operation control device 135 along the slide rail (not illustrated) to the left side in FIG. 1 to thereby separate the touch screen 131 from the user being seated on the seat unit 510.

The touch screen 131 displays rotational speed of the pedal 111; various input buttons such as an emergency stop button; and messages and information to the user such as the user's heart rate, the rotational speed of the pedal 111, remaining time for a task (described later), and the like. In addition, while the user performs the aerobic exercise of pedaling the pedal 111, the touch screen 131 provides questions to the user by displaying the questions on a task display part constituting a part of the touch screen 131, under control of the control device unit 136 (refer to FIG. 2). Furthermore, when the user taps a part of the question displayed on the touch screen 131, the touch screen 131 inputs the user's answer to the question and outputs the information about the answer as an electronic signal to the control device unit 136.

The question displayed on the touch screen 131 includes a question set for loaded exercise for cognitive function that causes the user perform a loaded exercise for cognitive function to thereby increase cerebral blood flow of the user. More specifically, the storage unit (ROM) of the control device unit 136 stores data of the question that causes the user answer by thinking with his/her brain while performing the aerobic exercise of pedaling the pedal 111, in a daily training described later.

As particular questions, for example, a plurality of kinds of questions requiring thinking power such as memory ability and calculation ability including: determination of values of numbers in a short time; memorization of an object displayed on the touch screen 131 for a short time; and count of the number of numerous cubes displayed on the touch screen 131, is classified and stored in the storage unit (ROM) of the control device unit 136. For these kinds of questions, questions of an elementary level, an intermediate level, an advanced level, and a master level are respectively classified and stored in the storage unit (ROM) of the control device unit 136.

Figure 3:
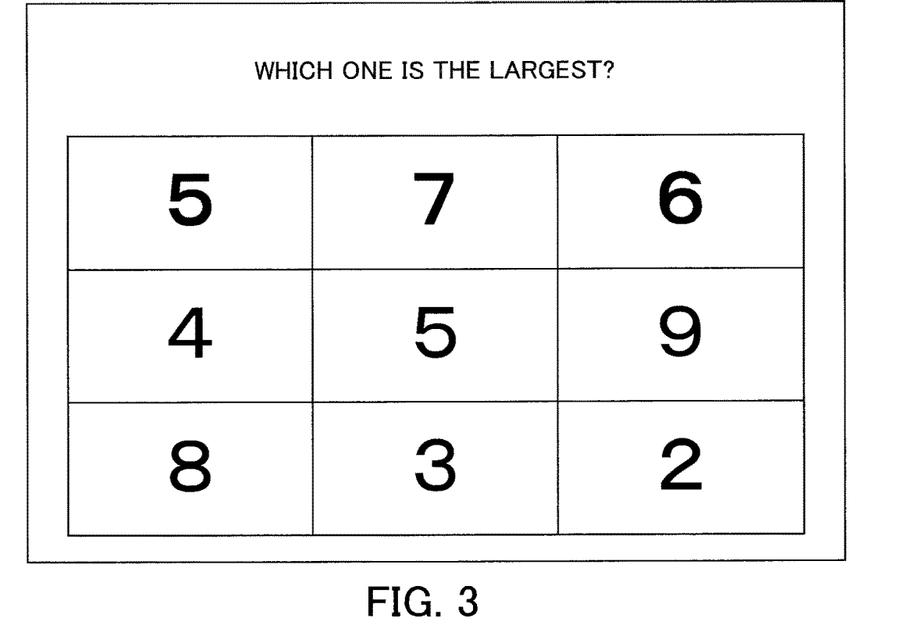
FIG. 3 is a diagram illustrating an example of a question displayed on a touch screen 131 of the aerobic exercise assistance apparatus 1 according to an embodiment of the present invention.

An example of a question of determination of values of numbers in a short time displayed on the touch screen 131 is as follows: for example, a question that causes a user select the greatest number among 9 single-digit numbers arranged in 3 by 3 matrix as illustrated in FIG. 3. The user taps the number he/she believes to be the greatest among the 9 numbers displayed on the touch screen 131. An answer to the question is thus input.

Figure 4:
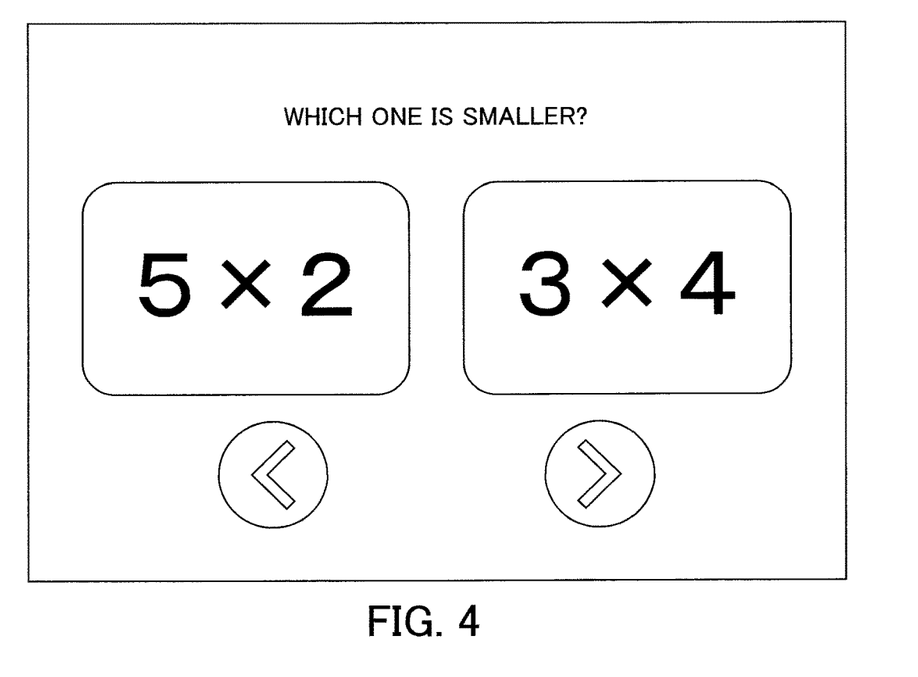
FIG. 4 is a diagram illustrating another example of a question displayed on a touch screen 131 of the aerobic exercise assistance apparatus 1 according to an embodiment of the present invention.

Another example of a question of determination of values of numbers in a short time displayed on the touch screen 131 is as follows: for example, a user selects a frame with a multiplication whose product is smaller among two frames with respective multiplications as illustrated in FIG. 4. The user selects a frame with the multiplication whose product he/she believes to be smaller, or an arrow displayed thereunder, among the two frames displayed on the touch screen 131. An answer to the question is thus input.

The time elapsed since the question is provided, that is, since the question is displayed on the touch screen 131, until the user answers by tapping the touch screen 131, is measured by the control device unit 136. The maximum time for answering the question is 90 seconds for each kind. In other words, the user answers as many questions as possible for a certain kind of questions, for example determination of values of numbers in a short time, within 90 seconds. When 90 seconds have elapsed since the first question of the certain kind of questions was displayed on the touch screen 131, the question being displayed is switched to a first question of another kind of questions regardless of presence of an answer from the user. In addition, the number of correct answers and the number of wrong answers are stored in the storage unit of the control device unit 136, and the control device unit 136 calculates correct answer ratio upon completion of each kind of questions.

The operation control device 135 controls the electronic device 120 to counteract rotation of the pedal 111, to thereby apply a load to the user who rotates the pedal 111. In other words, the electric motor generator 125 is driven such that the electronic device 120, the rotational shaft 121 and the rotational shaft pulley 122, the endless belt 124, the pedal pulley 113, the pedal shaft 112, and the pair of pedals 111 counteract movement of the user's legs and the like to continuously apply a load to the user's legs and the like. As a result, the user who rotates the pedal 111 performs an aerobic exercise of continuously moving his/her legs and the like. In other words, the electric motor generator 125 of the electronic device 120 operates as a dynamo upon application of a load. Intensity of the load applied by the electronic device 120 can be changed by the operation control device 135 controlling the electronic device 120 to change intensity of internal resistance of the electronic device 120 to thereby change the load.

The change in the internal resistance can be set to a predetermined value by an input from the user through the touch screen 131. The change in the internal resistance is made also by the control of the electronic device 120 by the control device unit 136. In other words, the control device unit 136 controls the electronic device 120 to change the load applied by the electronic device 120 as the load application driving unit, based on the user's correct answer ratio for the questions and timing of the answer to the question by the user. More specifically, when the user has finished answering all questions of one kind displayed on the touch screen 131, the control device unit 136 controls the electronic device 120 to increase or decrease the intensity of the internal resistance based on the correct answer ratio being calculated. Alternatively, when a patient with decreased physical strength uses the aerobic exercise assistance apparatus 1, the electric motor generator 125 of the electronic device 120 can also temporarily function as an electric motor that assists rotation of the pedal, when the load is being applied to the rotation of the pedal 111 and the like.

An upper part of the touch screen 131 includes an aroma diffusing unit 137 that diffuses aroma toward the user. The aroma diffusing unit 137 includes a slit-like opening portion formed on a front face and a rear face of the housing of the upper part of the touch screen 131 (not illustrated) and an aroma diffusing portion provided inside the housing (not illustrated). An aroma diffused from the aroma diffusing portion (not illustrated) flows out through the opening portion (not illustrated) and reaches the user. The user can, for example, perform the aerobic exercise in a relaxed state while smelling the aroma.

Figure 5:
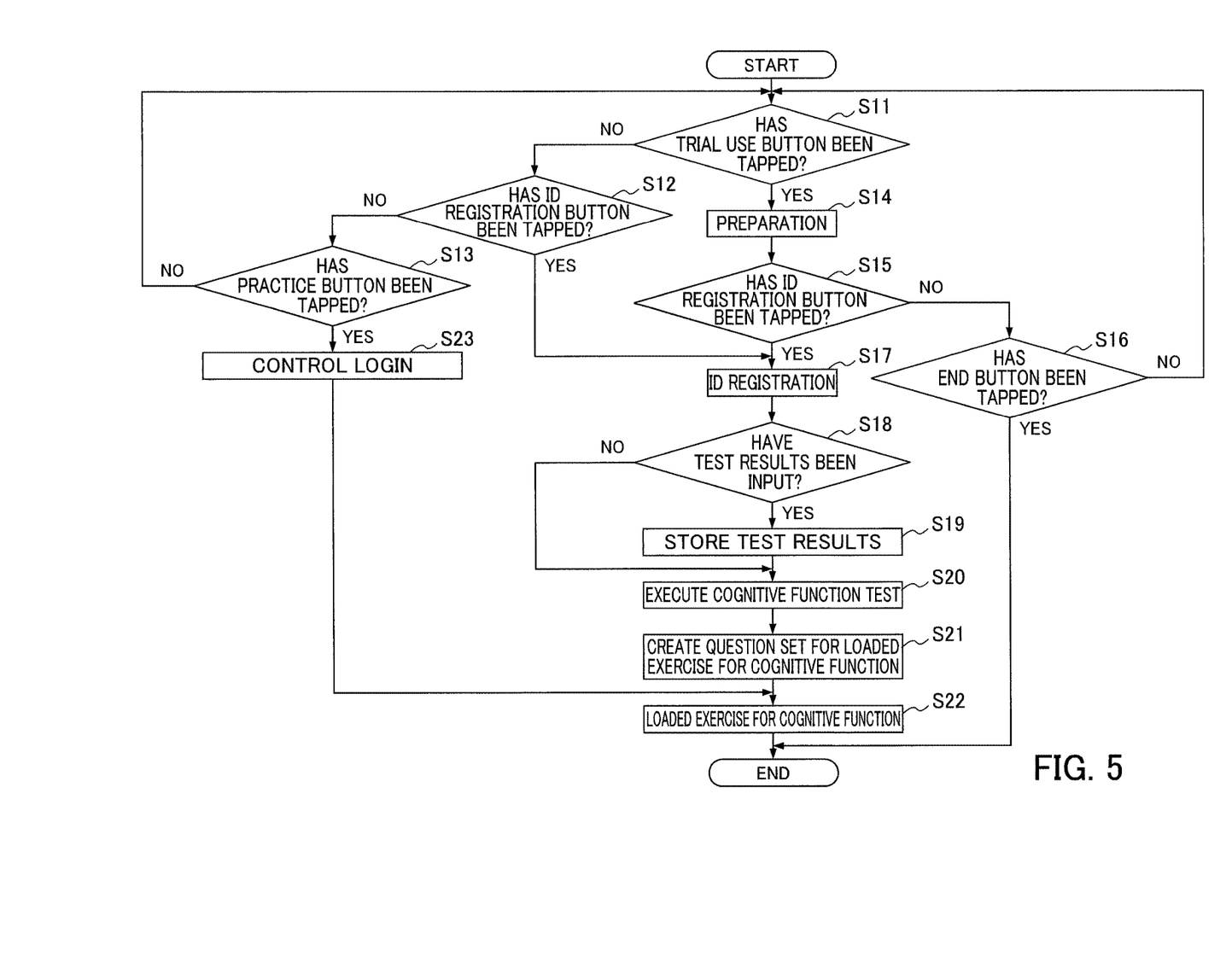
FIG. 5 is a flow chart showing an overall flow of a load application program for cognitive function, which is executed for a long time by using the aerobic exercise assistance apparatus 1 according to an embodiment of the present invention.

Next, an overall flow of the load application program for cognitive function, which is executed by using the aerobic exercise assistance apparatus 1 is explained. In the following explanation of the flow, the control by the control device unit 136 of the aerobic exercise assistance apparatus 1 is mainly explained. In the flow explained below, the user uses the aerobic exercise assistance apparatus 1 not by him/herself but with assistance of a trainer in view of safety.

First, an overall long-term continuous flow of a long-term continuous use of the aerobic exercise assistance apparatus 1 of more than six months since installation and the start of use of the aerobic exercise assistance apparatus 1 are explained. When the user uses the aerobic exercise assistance apparatus 1 for the first time, the user turns on the aerobic exercise assistance apparatus 1. Then, under the control of the touch screen 131 by the control device unit 136, the touch screen 131 displays a selection screen in which a trial use button for a user who does not have an ID registered with the aerobic exercise assistance apparatus 1, a practice button for a user who has an registered ID, an ID registration button, and an end button are displayed.

When the user taps on the trial use button (S11:YES), the processing by the control device unit 136 proceeds to S14. When the user taps on the ID registration button instead of the trial use button (S11:NO, S12:YES), the processing by the control device unit 136 proceeds to S17. When the user taps on the practice button instead of the trial use button or the ID registration button (S11:NO, S12:NO, S13:YES), the processing by the control device unit 136 proceeds to S23.

In S23, the control device unit 136 controls login. More specifically, input fields for a user ID and a password are displayed on the touch screen 131. The user inputs a user ID into the user ID field, and a login password into the login password field. In response, the processing by the control device unit 136 proceeds to S22.

In S14, the control device unit 136 controls the aerobic exercise assistance apparatus 1 to execute preparation. In the preparation, the control device unit 136 controls the touch screen 131 to display questions thereon, such that a user who uses the aerobic exercise assistance apparatus 1 for the first time can actually experience the loaded exercise for cognitive function by using the aerobic exercise assistance apparatus 1. This allows the user to answer the questions while preforming the aerobic exercise by pedaling the pedal 111. The processing by the control device unit 136 then proceeds to S15.

In S15, the control device unit 136 determines whether the ID registration button on the touch screen 131 has been tapped or not. If the control device unit 136 determines that the ID registration button has been tapped, the processing by the control device unit 136 proceeds to S17. If the control device unit 136 determines that the ID registration button has not been tapped, the processing by the control device unit 136 proceeds to S16.

In S16, the control device unit 136 determines whether the end button on the touch screen 131 has been tapped or not. If the control device unit 136 determines that the end button has been tapped, the processing by the control device unit 136 is terminated. If the control device unit 136 determines that the end button has not been tapped, the processing by the control device unit 136 returns to S11.

In S17, the control device unit 136 controls the touch screen 131 to display an ID registration window thereon. In response to this, the trainer who assists the user inputs required information for ID registration such as a login password, user's fingerprint information, and the like through the touch screen 131. Upon completion of input of the required information by the trainer, the processing by the control device unit 136 proceeds to S18.

In S18, the control device unit 136 determines whether a result of a test separately conducted on the user for checking the extent of dementia is to be input through the touch screen 131. More specifically, the control device unit 136 determines whether the result of the test has been input to the touch screen or a button for skipping the input displayed on the touch screen 131 has been tapped. If the result of the test has been input to the touch screen 131 (S18:YES), the processing by the control device unit 136 proceeds to S19. The test for checking the extent of dementia displayed by the user is conducted at a frequency of once every six months or so, and the input of the result of the test to the touch screen 131 also takes place at a frequency of once every six months or so. If the skip input button displayed on the touch screen 131 has been tapped (S18:NO), the processing by the control device unit 136 proceeds to S20. In S19, the control device unit 136 stores the test result being input to the touch screen 131 to a storage unit. The processing by the control device unit 136 then proceeds to S20.

In S20, the control device unit 136 controls the touch screen 131 to display a cognitive activity test on the touch screen 131, which is stored in the storage unit in advance, at a frequency of once every 30 days or so. Given this, on a day the cognitive activity test is not displayed on the touch screen 131, the processing by the control device unit 136 proceeds to S22 without going through S20 and S21. The cognitive activity test includes, for example, four kinds of tests: a test for checking memory defects; a test for checking an attentional function; a test for checking processing speed; and a test for checking visual space recognition.

The test for checking memory defects includes, for example, a test in which a user memorizes words displayed sequentially on the touch screen 131 each for a predetermined short period of time and then selects the words displayed from a table of words. The test for checking an attentional function includes, for example, a test in which a user taps a plurality of numerical characters and a plurality of hiragana characters randomly displayed on the touch screen 131 alternately in an ascending order. The test for checking processing speed includes, for example, a test in which a user selects and answers a specified shape displayed on the touch screen 131 from a plurality of shapes within a predetermined period of time. The test for checking visual space recognition includes, for example, a test of displaying a standard shape composed of a plurality of shapes on the touch screen 131 and then requesting a user to select a shape identical thereto from a plurality of options, the plurality of options being displayed on the touch screen 131 in orientations different from the standard shape. Upon completion of the cognitive activity test by the user, the control device unit 136 stores the result of the cognitive activity test to the storage unit. The processing by the control device unit 136 then proceeds to S21.

In S21, the control device unit 136 appropriately selects a question from a large number of questions stored in the storage unit of the control device unit 136 in advance based on the result of the test for checking the extent of dementia having been input from the touch screen 131 and stored to the storage unit in S18 and S19, and the result of the cognitive activity test having been stored in the storage unit in S20. The control device unit 136 thus creates a question set used in one set of the loaded exercise for cognitive function performed by the user once a day or so. The question set thus created is stored in the storage unit. The processing by the control device unit 136 then proceeds to S22.

Figure 6A:
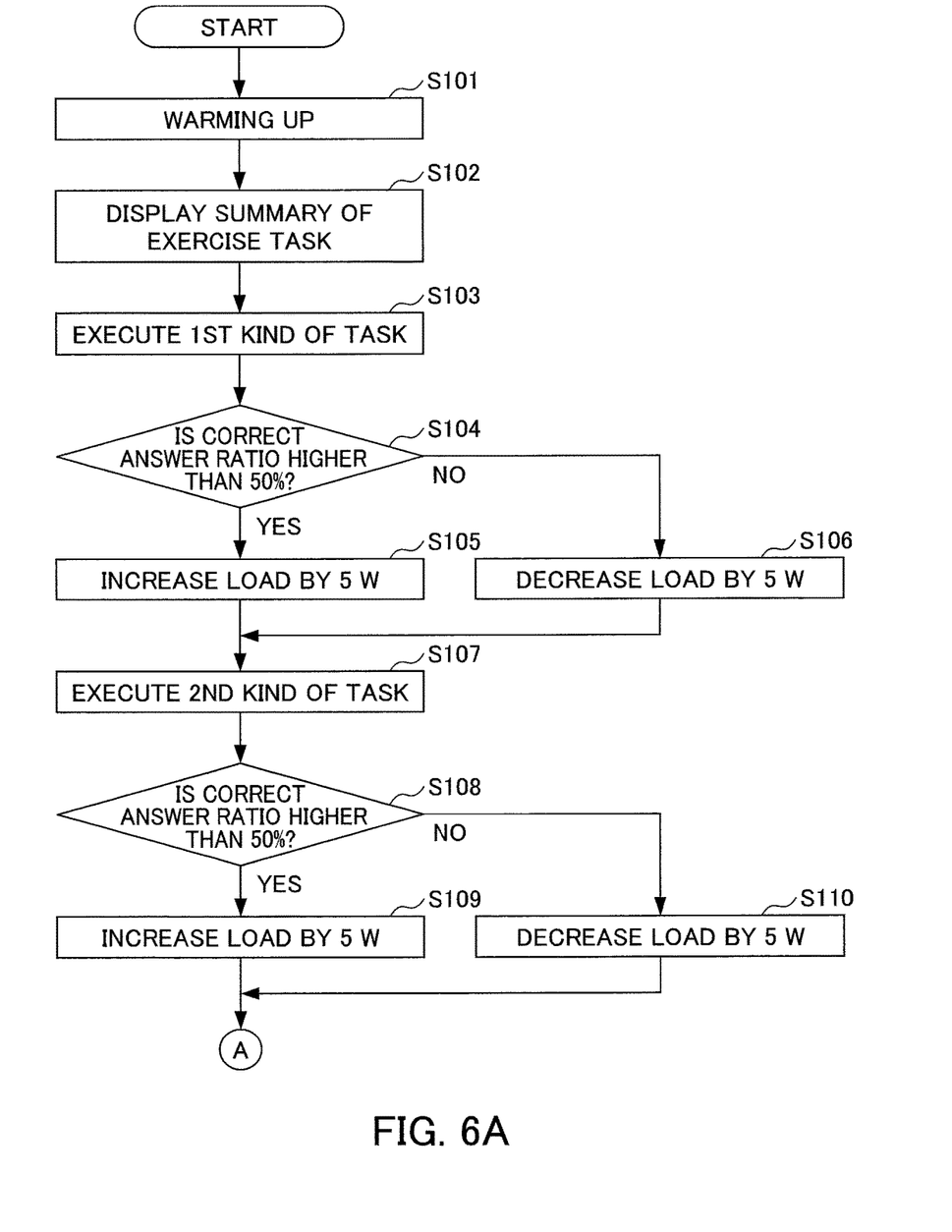
FIG. 6A is a flow chart showing a first half of a flow of training for a day (one set) in the load application program for cognitive function, which is executed for a long time by using the aerobic exercise assistance apparatus 1 according to an embodiment of the present invention.

In S22, the control device unit 136 controls the electronic device 120 and the touch screen 131 to allow the user to perform the loaded exercise for cognitive function performed once a day or so. More specifically, in S22, a control beginning from S101 shown in FIG. 6A is performed. First, in S101, the control device unit 136 controls the electronic device 120 to allow the user to warm up. The warming up is configured to allow the user to experience the speed of pedaling the pedal 111 by actually pedaling the pedal 111 while looking at a display content on the touch screen in the loaded exercise for cognitive function. The touch screen 131 displays a message indicating excessively high speed if the user pedals the pedal 111 too fast, and displays a message indicating excessively low speed if the user pedals the pedal 111 too slowly. The user adjusts the speed of pedaling the pedal 111 according to the messages and experiences the right speed of pedaling the pedal 111. A load applied to the pedal 111 is controlled by the control device unit 136 to, for example, 20 W. The processing by the control device unit 136 then proceeds to S102.

In S102, the control device unit 136 controls the touch screen 131 to display overviews of 6 kinds of tasks constituting the loaded exercise for cognitive function of an exercise program to be performed once by the user on the touch screen 131. More specifically, overviews of the 6 kinds of tasks, the order of the 6 kinds of tasks, a "level" of each task, time required for the user completing the task, and the like are displayed. The processing by the control device unit 136 then proceeds to S103.

In S103, the control device unit 136 controls the electronic device 120 and the touch screen 131 to execute a first kind of task. More specifically, the user operates the touch screen 131 to answer to questions displayed in the first kind of task, while pedaling the pedal 111 according to the speed of the pedal 111 experienced in the warming up. As the question in the first kind of task, for example, a question that causes a user select the greatest number among 9 single-digit numbers arranged in 3 by 3 matrix as shown above in FIG. 3 is displayed on the touch screen 131. The user taps the number he/she believes to be the greatest among the 9 numbers displayed on the touch screen 131. An answer to the question is thus input. The user answers as many such questions as possible within 90 seconds. The correct answer ratio to the questions is stored in the storage unit of the control device unit 136. The processing by the control device unit 136 then proceeds to S104.

In S104, the control device unit 136 determines whether the correct answer ratio stored in the storage unit of the control device unit 136 in S103 is at least 50% or not. In the case of the correct answer ratio stored in the storage unit of the control device unit 136 being at least 50%, the processing by the control device unit 136 proceeds to S105. In the case of the correct answer ratio stored in the storage unit of the control device unit 136 being lower than 50%, the processing by the control device unit 136 proceeds to S106.

In S105, the control device unit 136 controls the electronic device 120 to increase the load applied to the pedal 111 in the second kind of task to be executed next by 5 W with respect to the load applied to the pedal 111 in the first kind of task in S103. The processing by the control device unit 136 then proceeds to S107. On the other hand, in S106, the control device unit 136 controls the electronic device 120 to decrease the load applied to the pedal 111 in the second kind of task to be executed next by 5 W with respect to the load applied to the pedal 111 in the first kind of task in S103. The processing by the control device unit 136 then proceeds to S107. The load applied to pedal 111 is increased or decreased based on the timing at which the user has finished answering all of the first kind of questions. More particularly, immediately after the user finishes answering all of the first kind of questions, the control device unit 136 controls the electronic device 120 to increase or decrease the load applied to the pedal 111.

In S107, the control device unit 136 controls the electronic device 120 and the touch screen 131 to execute a second kind of task. More specifically, as the question in the second kind of task, for example, a question that causes a user provide an answer to a game of rock-paper-scissors so as to win (or lose) is displayed on the touch screen 131. The user selects and taps one of three shapes so as to beat (or lose to) a shape displayed on the touch screen 131. An answer to the question is thus input. The user answers as many such questions as possible within 90 seconds. The correct answer ratio to the questions is stored in the storage unit of the control device unit 136. The processing by the control device unit 136 then proceeds to S108.

In S108, the control device unit 136 determines whether the correct answer ratio stored in the storage unit of the control device unit 136 in S107 is at least 50% or not. In the case of the correct answer ratio stored in the storage unit of the control device unit 136 being at least 50%, the processing by the control device unit 136 proceeds to S109. In the case of the correct answer ratio stored in the storage unit of the control device unit 136 being lower than 50%, the processing by the control device unit 136 proceeds to S110.

In S109, the control device unit 136 controls the electronic device 120 to increase the load applied to the pedal 111 in the second kind of task to be executed next by 5 W with respect to the load applied to the pedal 111 in the second kind of task in S107. The processing by the control device unit 136 then proceeds to S111. On the other hand, in S110, the control device unit 136 controls the electronic device 120 to decrease the load applied to the pedal 111 in the second kind of task to be executed next by 5 W with respect to the load applied to the pedal 111 in the second kind of task in S107. The processing by the control device unit 136 then proceeds to S111. The load applied to pedal 111 is increased or decreased based on the timing at which the user has finished answering all of the second kind of questions. More particularly, immediately after the user finishes answering all of the second kind of questions, the control device unit 136 controls the electronic device 120 to increase or decrease the load applied to the pedal 111.

Figure 6B:
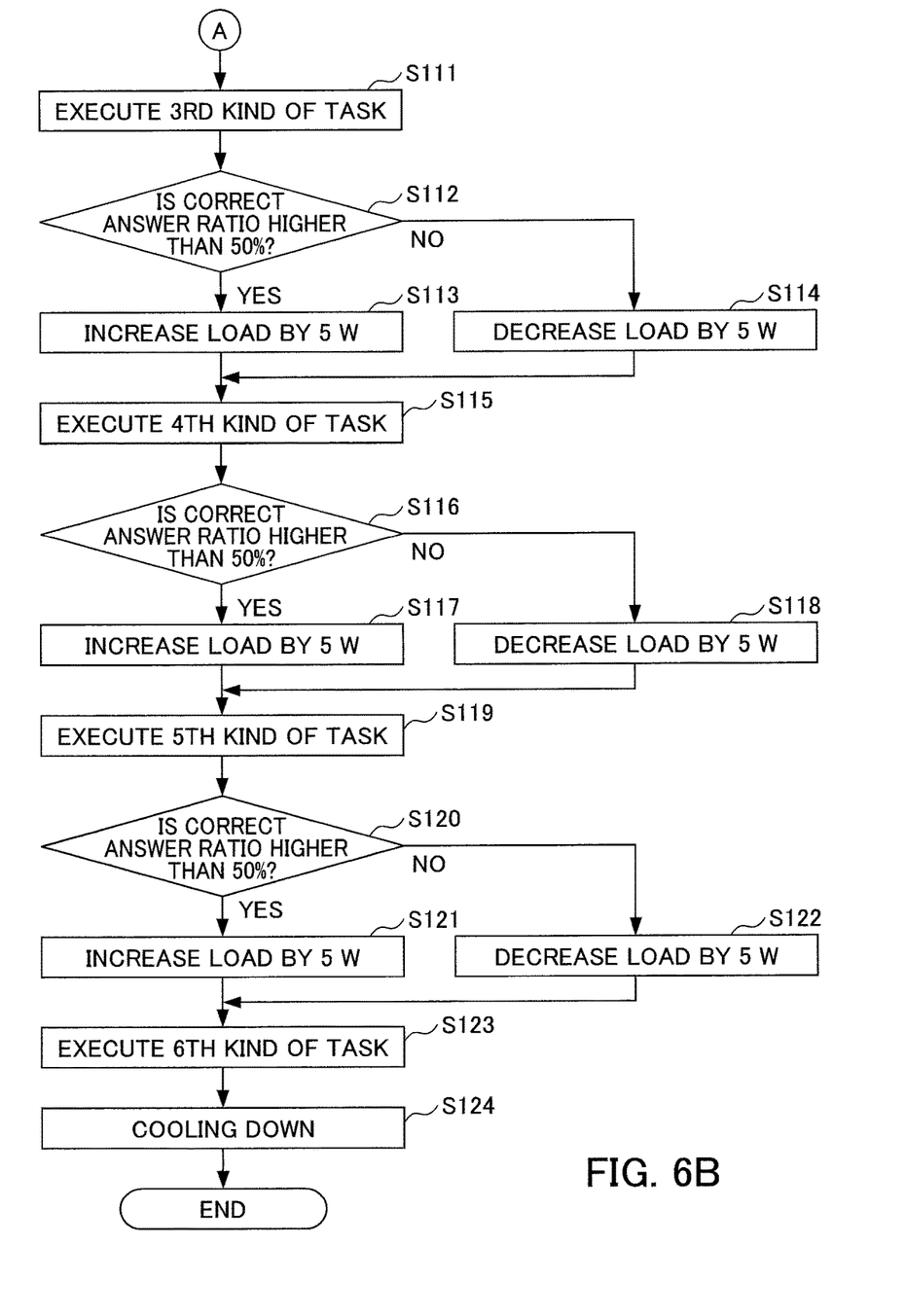
FIG. 6B is a flow chart showing a second half of a flow of training for a day (one set) in the load application program for cognitive function, which is executed for a long time by using the aerobic exercise assistance apparatus 1 according to an embodiment of the present invention.

Hereinafter, in S111 to S114, the control device unit 136 controls for a third kind of task as in the above described S103 to S106 and S107 to S110. In addition, in S115 to S118, the control device unit 136 controls for a fourth kind of task as in the above described S103 to S106 and S107 to S110. Furthermore, in S119 to S122, the control device unit 136 controls for a fifth kind of task as in the above described S103 to S106 and S107 to S110.

And then, in S123, the control device unit 136 controls the electronic device 120 and the touch screen 131 to execute a sixth kind of task. More specifically, as the question in the sixth kind of task, for example, a question that causes a user to select and answer a multiplication whose product is smaller among two multiplications is displayed on the touch screen 131. The user taps the multiplication whose product he/she believes to be smaller among two multiplications. An answer to the question is thus input. The user answers as many such questions as possible within 90 seconds. The correct answer ratio to the questions is stored in the storage unit of the control device unit 136. The processing by the control device unit 136 then proceeds to S124.

In S124, the control device unit 136 controls the electronic device 120 and the touch screen 131 to allow the user to do a cool-down. The load applied to the pedal 111 is controlled by the control device unit 136 to, for example, 20 W, and the user does the cool-down by pedaling the pedal 111 for a predetermined period of time while looking at a radar chart showing a result of the answers to the questions. If the correct answer ratio of the user is higher than 70% twice in a row (for two days in a row) for each kind of task, the control device unit 136 stores in the storage unit a piece of information indicating that the level of questions for the kind of task is to be raised by one in the next set (next day). On the contrary, if the correct answer ratio of the user is lower than 30% twice in a row (for two days in a row (previous day and present day)), the control device unit 136 stores in the storage unit a piece of information indicating that the level of questions for the kind of task is to be lowered by one in the next set (next day). The processing by the control device unit 136 is then terminated.

S101 to S124 are performed once a day; the cognitive function test of S20 is performed once a month; and the question set used in a course of loaded exercise for cognitive function to be performed by the user once a day or so in the next one month is created in S21. In addition, a result of the test for checking the extent of dementia, which is separately conducted on the user once every six months, is input from the touch screen 131 in S19. The question set is created in S21 taking into consideration the result of the test being input in S19.

According to the aerobic exercise assistance apparatus 1 according to the present embodiment configured as described above, the following effects can be obtained.

The aerobic exercise assistance apparatus 1 comprises: the electronic device 120 as the load application driving unit that is driven to apply a load continuously to a part or an entirety of a user's body against a movement of the part or the entirety of the body, in order to cause a user perform an aerobic exercise by continuously moving the part or the entirety of the body; the control device unit 136 constituting the control unit that controls the load application driving unit to change the load applied by the load application driving unit; and the touch screen 131 as the input/output unit that, under control by the control unit, gives the user a question and accepts an input of an answer from the user to the question while the user performs the aerobic exercise. The control device unit 136 controls the electronic device 120 to change the load applied by the electronic device 120, based on a correct answer ratio of the user for the question and timing of the answer to the question by the user.

This configuration allows a user to perform an aerobic exercise by pedaling the pedal 111 while making full use of memory and thinking power by answering the questions. In other words, the user can perform a loaded exercise for cognitive function by actively memorizing and thinking while performing the aerobic exercise, and thus can increase the cerebral blood flow. Consequently, the dual-task performance ability, which is recently gaining attention, in other words the ability of performing an action while distributing attention to various stimuli, can be actively trained, deterioration of the dual-task performance ability can be suppressed, and deterioration of the cognitive function can be suppressed.

In addition, the electronic device 120 as the load application driving unit, and the control device unit 136 as the control unit constitute an ergometer. This configuration allows a user to easily make full use of memory and thinking power by answering the questions while performing the aerobic exercise, at home.

Furthermore, the control device unit 136 as the control unit, immediately after the user answers the questions at a predetermined correct answer ratio, changes the load applied by the electronic device 120 as the load application driving unit. This configuration allows switching of the load applied to the pedal 111 by the electronic device 120 at the timing of switching of the kind of questions, by calculating the correct answer ratio for each kind of questions while the user is answering various kinds of questions. As a result, in order to respond to an unexpected change in the load of the pedal 111, the user is forced to exert an exercise capacity different from the previous one by changing the force to pedal the pedal 111. As a result, reduction in cerebral blood flow due to habituation to a predetermined exercise pattern in a case in which the user exercises in the predetermined exercise pattern can be prevented.

Moreover, the question includes a question set for loaded exercise for cognitive function that causes the user perform a loaded exercise for cognitive function to thereby increase cerebral blood flow of the user. This configuration allows the user to efficiently exert the thinking power and the memory ability by answering the questions while performing the aerobic exercise by pedaling the pedal 111, thereby providing the loaded exercise for cognitive function and increasing the cerebral blood flow.

The seat unit 510 allowing the user to perform the aerobic exercise in a seated position is further provided, the seat unit 510 having the armrest 513. This configuration can prevent the user seated on the seat component 512 from falling from the seat component 512.

A fingerprint authentication device that can identify a predetermined user is preferably provided. This configuration can, in a case in which a plurality of users use the aerobic exercise assistance apparatus 1, prevent errors such as applying a "level" of the predetermined user having already used the aerobic exercise assistance apparatus 1 to other users.

An aroma diffusing unit 137 that diffuses aroma toward the user is further provided. This configuration allows the user to perform the aerobic exercise in a relaxed state or in a concentrated state while smelling the aroma, depending on the type of the aroma.

The seat unit 510 allowing the user to perform the aerobic exercise in a seated position is further provided. The seat unit 510 is supported by a slide rail, so as to be movable with respect to the slide rail, and has the slide lock lever 511 as a switching member that switches between a movable state and a fixed state with respect to the slide rail. This configuration allows the user in the seated position to switch between the movable state and the fixed state of the seat unit 510 with respect to the slide rail. Given the above, even in a case in which an elderly person uses the aerobic exercise assistance apparatus at home, risk of the user falling can be suppressed while allowing the user to move the seat unit 510 with respect to the slide rail by him/herself, to position the seat unit 510 at an optimal position, and to be seated on the seat unit 510. In addition, the user in the seated position can move the seat unit 510 with respect to the slide rail by him/herself and get off the seat unit 510.

The present invention is not limited to the above described embodiment, and may be modified within a technical scope specified in the Claims. For example, in the present embodiment, the aerobic exercise is performed mainly by continuously moving the lower body by pedaling the pedal 111 of the aerobic exercise assistance apparatus 1 constituted by an ergometer; however the present invention is not limited thereto. The aerobic exercise can be performed in any manner of moving a part or an entirety of the user's body.

In addition, in the present embodiment, the electronic device 120 is controlled to calculate the correct answer ratio for the first kind of task when the user has answered all of a plurality of questions of the first kind of task, and then, based on the correct answer ratio thus calculated, to increase the load applied to the pedal 111 in the second kind of task to be executed next by 5 W with respect to the load applied to the pedal 111 in the first kind of task in S103; however, the present invention is not limited thereto.

In other words, the load applied by the load application driving unit may be changed any way based on the user's correct answer ratio to the questions and on the timing of the user's answer to the question. For example, the correct answer ratio for the answered questions can be calculated and determination of whether the correct answer ratio is at least a predetermined value or not can take place after each answer to the question. Then, if the correct answer ratio is at least the predetermined value, the electronic device 120 can be controlled to increase the load applied to the pedal 111 by a predetermined amount immediately after the answer to the question, and if the correct answer ratio is lower than the predetermined value, the electronic device 120 can be controlled to decrease the load applied to the pedal 111 by a predetermined amount immediately after the answer to the question.

Furthermore, in the present embodiment, if the correct answer ratio for one kind of task is at least 50%, which is a predetermined value, the load of the pedal 111 for a user answering questions of the subsequent kind of task is increased, while if the correct answer ratio for one kind of task is lower than 50%, which is the predetermined value, the load of the pedal 111 for a user answering questions of the subsequent kind of task is decreased; however, the present invention is not limited thereto. For example, the load of the pedal 111 may be decreased if the correct answer ratio is at least 50%, which is the predetermined value, and the load of the pedal 111 may be increased if the correct answer ratio is at least 50%, which is a predetermined value.

In addition, in the present embodiment: the main body rear part 50 can be guided by the slide rail 101 to separate from/approach the main body front part 10; the seat unit 510 can be guided by the slide rail (not illustrated) to move vertically with respect to the main body rear part 50; and the operation control device 135 including the touch screen 131 can be guided by the slide rail (not illustrated) to move forward/backward, each manually; however, the present invention is not limited thereto. For example, these movements can be realized electrically, and positions upon use of the main body rear part 50, the seat unit 510, and the operation control device 135 for a user may be stored in the control device unit 136 upon registration of the user's ID. And then, the main body rear part 50, the seat unit 510, and the operation control device 135 may be moved automatically to the stored positions for the user when the user logs in.

Furthermore, in the present embodiment, the result of the test separately conducted on the user for checking the extent of dementia is input in S19; however, the present invention is not limited to this configuration. For example, a test for checking the extent of dementia may be stored in the storage unit of the control device unit 136 in advance and then displayed on the touch screen 131, and the user's result of the test may be stored in the storage unit of the control device unit 136.

In addition, in the present embodiment, for each kind of task, if the correct answer ratio of the user is higher than 70% twice in a row (for two days in a row (previous day and present day)), the control device unit 136 stores a piece of information indicating that the level of questions for the kind of task is to be raised by one in the next set (next day). On the contrary, if the correct answer ratio of the user is lower than 30% twice in a row (for two days in a row (previous day and present day)), the control device unit 136 stores a piece of information indicating that the level of questions for the kind of task is to be lowered by one in the next set (next day); however, the present invention is not limited thereto.

For example, the level may be divided into an elementary level, an intermediate level, an advanced level, and a master level; however, each of these levels may be further divided into A, B, and C. The level of the questions to be provided the next day may also be determined as follows, based on the correct answer ratio of the current course (today) and an average of the correct answer ratio of the last three courses.

For example, if the correct answer ratio of the user on the first day is no higher than 30% (30 points or lower out of 100), the level of the question of this kind of task to be provided next time (next day) is "elementary A". If the correct answer ratio of the user on the first day is at least 31% (31 points or higher out of 100) and no higher than 70% (70 points or lower out of 100), the level of the question of this kind of task to be provided next time (next day) is "intermediate A". If the correct answer ratio of the user on the first day is at least 71% (71 points or higher out of 100), the level of the question of this kind of task to be provided next time (next day) is "advanced A".

Thereafter, provided that the today's level is "elementary A", if the average of the correct answer ratio of the last three courses is at least 70% (70 points or higher out of 100), the level of the question of this kind of task to be provided next time (next day) is "advanced B".

Provided that the today's level is "intermediate A", if the average of the correct answer ratio of the last three courses is at least 70% (70 points or higher out of 100), the level of the question of this kind of task to be provided next time (next day) is "intermediate B". On the contrary, if the average of the correct answer ratio of the last three courses is no higher than 30% (30 points or lower out of 100), the level of the question of this kind of task to be provided next time (next day) is "elementary C".

Provided that the today's level is "advanced A", if the average of the correct answer ratio of the last three courses is at least 70% (70 points or higher out of 100), the level of the question of this kind of task to be provided next time (next day) is "advanced B". On the contrary, if the average of the correct answer ratio of the last three courses is no higher than 30% (30 points or lower out of 100), the level of the question of this kind of task to be provided next time (next day) is "intermediate C".

Provided that the today's level is "master A", if the average of the correct answer ratio of the last three courses is at least 70% (70 points or higher out of 100), the level of the question of this kind of task to be provided next time (next day) is "master B". On the contrary, if the average of the correct answer ratio of the last three courses is no higher than 30% (30 points or lower out of 100), the level of the question of this kind of task to be provided next time (next day) is "advanced C".

Provided that the today's level is "elementary B", if the average of the correct answer ratio of the last three courses is at least 70% (70 points or higher out of 100), the level of the question of this kind of task to be provided next time (next day) is "elementary C". On the contrary, if the average of the correct answer ratio of the last three courses is no higher than 30% (30 points or lower out of 100), the level of the question of this kind of task to be provided next time (next day) is "elementary A".

Provided that the today's level is "intermediate B", if the average of the correct answer ratio of the last three courses is at least 70% (70 points or higher out of 100), the level of the question of this kind of task to be provided next time (next day) is "intermediate C". On the contrary, if the average of the correct answer ratio of the last three courses is no higher than 30% (30 points or lower out of 100), the level of the question of this kind of task to be provided next time (next day) is "intermediate A".

Provided that the today's level is "advanced B", if the average of the correct answer ratio of the last three courses is at least 70% (70 points or higher out of 100), the level of the question of this kind of task to be provided next time (next day) is "advanced C". On the contrary, if the average of the correct answer ratio of the last three courses is no higher than 30% (30 points or lower out of 100), the level of the question of this kind of task to be provided next time (next day) is "advanced A".

Provided that the today's level is "master B", if the average of the correct answer ratio of the last three courses is at least 70% (70 points or higher out of 100), the level of the question of this kind of task to be provided next time (next day) is "master C". On the contrary, if the average of the correct answer ratio of the last three courses is no higher than 30% (30 points or lower out of 100), the level of the question of this kind of task to be provided next time (next day) is "master A".

Alternatively, provided that the today's level is "elementary C", if the average of the correct answer ratio of the last three courses is at least 70% (70 points or higher out of 100) and the best score of the test is at least 31, the level of the question of this kind of task to be provided next time (next day) is "intermediate A". On the contrary, if the average of the correct answer ratio of the last three courses is no higher than 30% (30 points or lower out of 100), the level of the question of this kind of task to be provided next time (next day) is "elementary B".

Provided that the today's level is "intermediate C", if the average of the correct answer ratio of the last three courses is at least 70% (70 points or higher out of 100) and the best score of the test is at least 71, the level of the question of this kind of task to be provided next time (next day) is "advanced A". On the contrary, if the average of the correct answer ratio of the last three courses is no higher than 30% (30 points or lower out of 100), the level of the question of this kind of task to be provided next time (next day) is "elementary B".

Provided that the today's level is "advanced C", if the average of the correct answer ratio of the last three courses is at least 70% (70 points or higher out of 100) and the best score of the test is at least 81, the level of the question of this kind of task to be provided next time (next day) is "master A". On the contrary, if the average of the correct answer ratio of the last three courses is no higher than 30% (30 points or lower out of 100), the level of the question of this kind of task to be provided next time (next day) is "advanced B".

Provided that the today's level is "master C", if the average of the correct answer ratio of the last three courses is no higher than 30% (30 points or lower out of 100), the level of the question of this kind of task to be provided next time (next day) is "master B".

Furthermore, configurations of units of the aerobic exercise assistance apparatus are not limited to those of the units of the aerobic exercise assistance apparatus 1 according to the present embodiment. For example, the control of the amount of load is not limited to that of the present embodiment. The amount of load may also be controlled according to well-known methods such as the Karvonen Formula and the BORG scale, based on a heart rate detected by a wrist-band sensor.

Although the electronic device 120 and the control device unit 136 collectively serving as the load application driving unit constitute an ergometer in the present embodiment, the present invention is not limited thereto. For example, the load application driving unit can constitute a treadmill instead of the ergometer. In addition, although the aerobic exercise assistance apparatus 1 is used for a loaded exercise for cognitive function in the present embodiment, the present invention is not limited thereto. For example, the aerobic exercise assistance apparatus 1 may also be used for brain development and physical strength enhancement for children.

EXPLANATION OF REFERENCE NUMERALS 1 aerobic exercise assistance apparatus
110 pedal driving unit (load application driving unit)
120 electronic device (load application driving unit)
131 touch screen (input/output unit)
136 control device unit (control unit)
137 aroma diffusing unit
510 seat unit
511 slide lock lever (switching member)
513 armrest

The invention claimed is:

1. An aerobic exercise assistance apparatus comprising:
a load application driving unit that is driven to apply a load continuously to a part or an entirety of a user's body against a movement of the part or the entirety of the body, in order to cause a user perform an aerobic exercise by continuously moving the part or the entirety of the body;
a control unit that controls the load application driving unit to change the load applied by the load application driving unit; and
an input/output unit that, under control by the control unit, presents the user a question and accepts an input of an answer from the user to the question while the user performs the aerobic exercise,
wherein the control unit controls the load application driving unit to change the load applied by the load application driving unit, based on a correct answer ratio of the user for the question and timing of the answer to the question by the user.

2. The aerobic exercise assistance apparatus according to claim 1, wherein the load application driving unit and the control unit constitute an ergometer.

3. The aerobic exercise assistance apparatus according to claim 1, wherein the control unit changes the load applied by the load application driving unit immediately after the user answers the question at a predetermined correct answer ratio.

4. The aerobic exercise assistance apparatus according to claim 1, wherein the question comprises a question set for loaded exercise for cognitive function that causes the user perform a loaded exercise for cognitive function to thereby increase cerebral blood flow of the user.

5. The aerobic exercise assistance apparatus according to claim 1 further comprising a seat portion that allows the user to perform the aerobic exercise in a seated position,
wherein the seat portion comprises an armrest.

6. The aerobic exercise assistance apparatus according to claim 1 further comprising a fingerprint authentication device that can identify a predetermined user.

7. The aerobic exercise assistance apparatus according to claim 1 further comprising an aroma diffusing unit that diffuses aroma toward the user.

8. The aerobic exercise assistance apparatus according to claim 1 further comprising a seat portion that allows the user to perform the aerobic exercise in a seated position,
wherein the seat portion is supported by a slide rail so as to be movable with respect to the slide rail, and comprises a switching member that switches between a movable state and a fixed state with respect to the slide rail.

* * * * *